(12) United States Patent
Suzuki

(10) Patent No.: US 8,057,525 B2
(45) Date of Patent: Nov. 15, 2011

(54) BEAUTY DEVICE

(75) Inventor: Shuhei Suzuki, Tokyo (JP)

(73) Assignee: Futek, Inc., Tokyo (JP)

( * ) Notice: Subject to any disclaimer, the term of this patent is extended or adjusted under 35 U.S.C. 154(b) by 401 days.

(21) Appl. No.: 11/236,817

(22) Filed: Sep. 28, 2005

(65) Prior Publication Data
US 2007/0016269 A1 Jan. 18, 2007

(30) Foreign Application Priority Data
Jul. 12, 2005 (JP) ................. 2005-202434

(51) Int. Cl.
*A61N 5/06* (2006.01)
(52) U.S. Cl. .................. 607/88; 607/89; 607/95; 606/2; 606/19

(58) Field of Classification Search ............ 607/88, 607/104, 108–112, 114
See application file for complete search history.

(56) References Cited

U.S. PATENT DOCUMENTS

| | | | | | |
|---|---|---|---|---|---|
| 5,913,883 | A * | 6/1999 | Alexander et al. | | 607/88 |
| 6,238,425 | B1 * | 5/2001 | Thiberg | | 607/88 |
| 6,290,713 | B1 * | 9/2001 | Russell | | 607/88 |
| 6,860,896 | B2 * | 3/2005 | Leber et al. | | 607/1 |
| 6,896,693 | B2 * | 5/2005 | Sullivan | | 607/91 |
| 2004/0260365 | A1 * | 12/2004 | Groseth et al. | | 607/88 |

* cited by examiner

*Primary Examiner* — Aaron Roane
(74) *Attorney, Agent, or Firm* — Wenderoth, Lind & Ponack, L.L.P.

(57) ABSTRACT

A beauty device includes a light irradiation section having a blue LED, a yellow LED, a red LED, and near infrared LED each of which emits light with a predetermined wavelength to a face A, and an oxygen supply section 2 that supplies oxygen to the face A.

8 Claims, 5 Drawing Sheets

BEAUTY DEVICE

BACKGROUND OF THE INVENTION

1. Field of the Invention

The present invention relates to a beauty device that irradiates human skin with light of a predetermined wavelength, and more particularly to a beauty device that has effects on removal of face blemishes.

2. Description of the Related Art

Various types of beauty devices that have effects on facial beauty treatment have been conventionally known. For example, Unexamined Japanese Patent Publication 2000-217938 discloses that human skin is irradiated with a laser beam to obtain skin beauty effects.

However, the technique disclosed in the above patent publication is limited to one using the laser beam irradiation and there is a fixed limitation in the skin beauty effects. Accordingly, the beauty device, which is more excellent in the skin beauty effects, has been expected.

SUMMARY OF THE INVENTION

The present invention has been made with consideration given to the aforementioned circumstances and an object of the present invention is to provide a beauty device that is excellent in skin beauty effects.

A beauty device according to a first aspect of the present invention includes a light irradiation section that irradiates a skin surface with light of a predetermined wavelength; and an oxygen supply section that supplies oxygen to the skin surface.

According to the main aspect of the present invention, since the oxygen supply section is formed in addition to the light irradiation section, sufficient skin beauty effects can be exerted by the synergistic result of the light from the light irradiation section and the oxygen from the oxygen supply section as compared with the beauty device including only the light irradiation section. In other words, the oxygen is supplied to the skin from the oxygen supply section, so that the skin is activated and fine particles such as powder of cosmetics are easily introduced into the skin and the concentration of oxygen in the skin is increased. As a result, the skin can be minus-ionized to obtain excellent skin beauty effects.

In the first aspect of the present invention, the beauty device desirably includes a mask that covers a human face. The light irradiation section and the oxygen supply section are desirably formed on the mask to perform light irradiation and oxygen supply to the face. Accordingly, the light irradiation section, which covers the face, and the oxygen supply section are formed, so that oxygen can be taken from the oxygen supply section and introduced into the human body. As a result, the oxygen is delivered to the details of cells to allow metabolism to be improved from the inner portion of the body, thereby enabling to exert more excellent skin beauty effects.

Moreover, in the first aspect of the present invention, the number of light irradiation sections is desirably multiple, and an oxygen supply port of the oxygen supply section is desirably formed between the light irradiation sections. Accordingly, since the oxygen supply port is formed between the light irradiation sections, oxygen can be efficiently supplied to the light irradiating portion on the skin surface.

Furthermore, the light irradiation section desirably includes multiple light emitting diodes each having a different wavelength. Accordingly, since the multiple light emitting diodes are provided, a fibroblast is stimulated by light irradiation with two or more wavelengths to make it possible to reduce blemishes and wrinkles sufficiently and exert the excellent skin beauty effects.

Moreover, the light irradiation section desirably includes a blue light emitting diode that emits a blue light, a yellow light emitting diode that emits a yellow light, a red light emitting diode that emits a red light, and a near infrared light emitting diode that emits near infrared light. The yellow light emitting diode, the red light emitting diode and the near infrared light emitting diode are desirably arranged to surround the blue light emitting diode.

In this case, nerve block is stimulated by light with four wavelengths where the blue light is added to the yellow light, the red light, and the near infrared light each having good permeability, thereby allowing an efficient reduction in blemishes and wrinkles. Also, light of multiple kinds can be uniformly and sufficiently interfered to perform irradiation, thereby making it possible to obtain more excellent skin beauty effects such as improvement in a pimpled skin, moisture effect, improvement in a red face, a reduction in pores of the skin. Moreover, since no ultraviolet rays are emitted, a fixed skill (with expert knowledge) is not required for using the device, allowing the safe use of the device at home.

Furthermore, in the first aspect of the present invention, oxygen that is supplied by the oxygen supply section desirably has a concentration in a range of 30 volume % to 50 volume %. As a result of the experiment, when the concentration is below 30 volume %, much time is required to obtain sufficient skin beauty effects. While, when the concentration exceeds 50 volume %, no difference is found out in the skin beauty effects. Accordingly, the concentration of oxygen is set to 30 volume % to 50 volume %, thereby making it possible to obtain sufficient skin beauty effects with efficient concentration of oxygen for a short time. Also, the oxygen range, which does not exceed 50 volume %, is desirable in view of the treatment of oxygen.

Furthermore, the light emitting diode desirably blinks at random or at predetermined timing. Accordingly, since the light emitting diode blinks at random or at predetermined timing, it was more effective to obtain skin beauty effects.

Furthermore, the light emitting diode desirably blinks with a frequency of 1 Hz to 2 kHz. The reason why the frequency ranges 1 Hz to 2 kHz in this way is as follows. Namely, when the frequency is below 1 Hz, it takes too much time to obtain sufficient skin beauty effects. While, when the frequency exceeds 2 kHz, no difference is found out in the skin beauty effects.

BRIEF DESCRIPTION OF THE DRAWINGS

These objects and other objects and advantages of the present invention will become more apparent upon reading of the following detailed description and the accompanying drawings in which.

DETAILED DESCRIPTION OF THE PREFERRED EMBODIMENT

An embodiment of the present invention will be explained with reference to the accompanying drawings.

Figure 1:
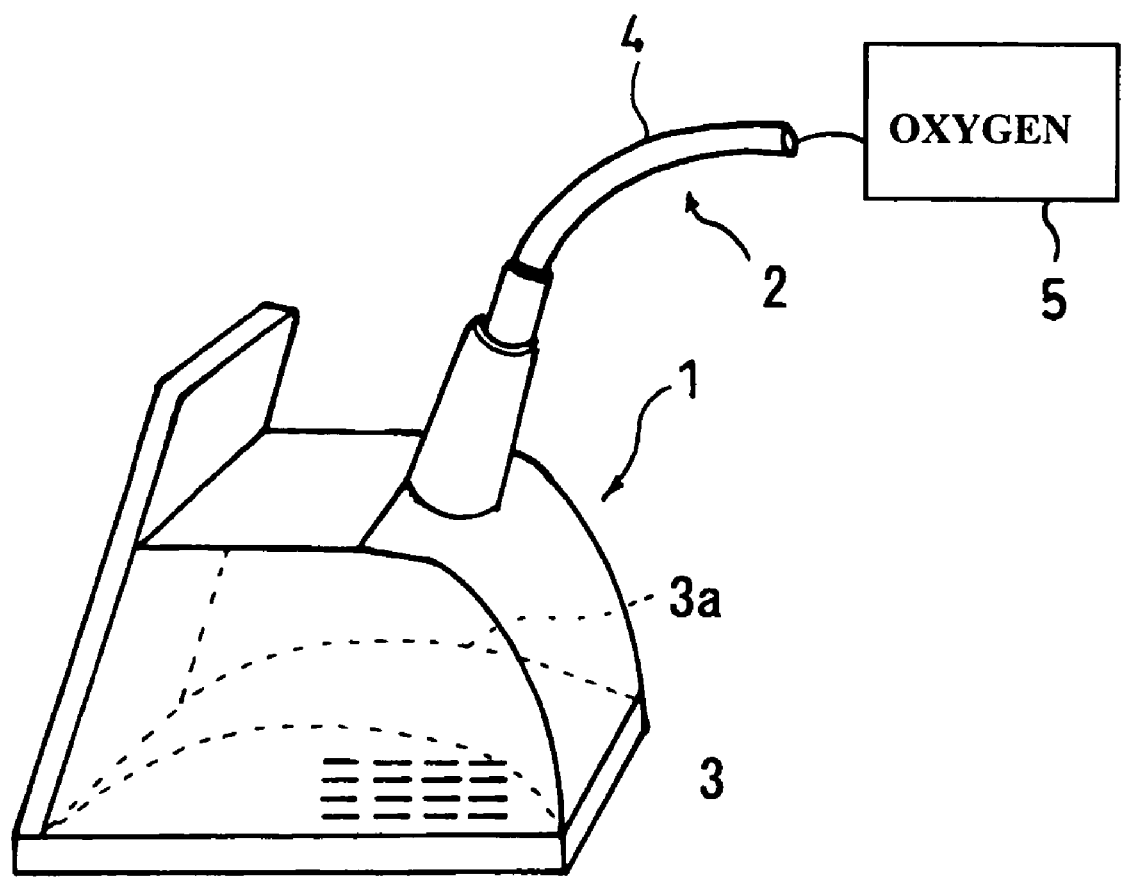
FIG. 1 is a perspective view of a beauty device according to an embodiment of the present invention.
Figure 2:
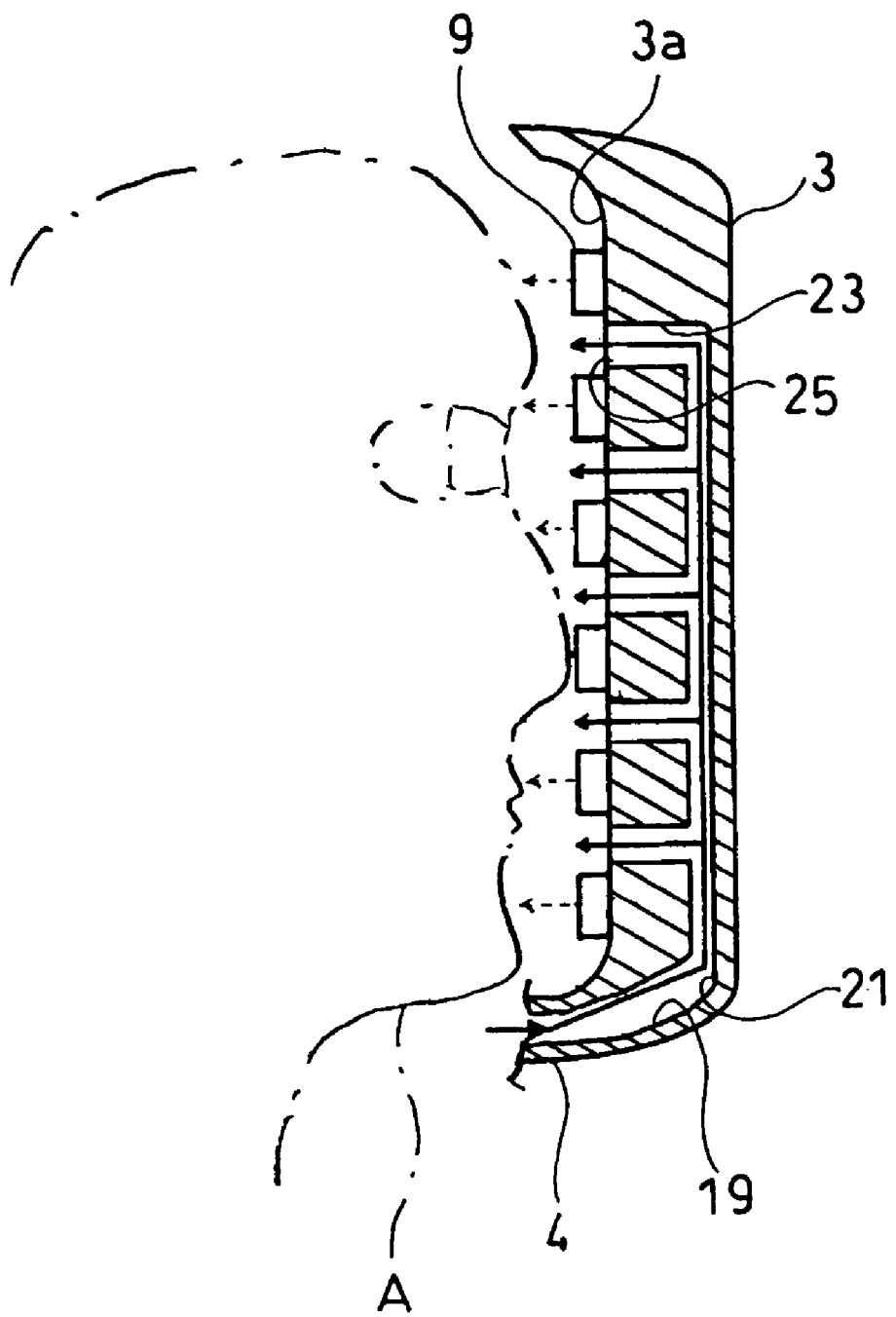
FIG. 2 is a cross sectional view illustrating an outline of a mask of the beauty device of FIG. 1.
Figure 3:
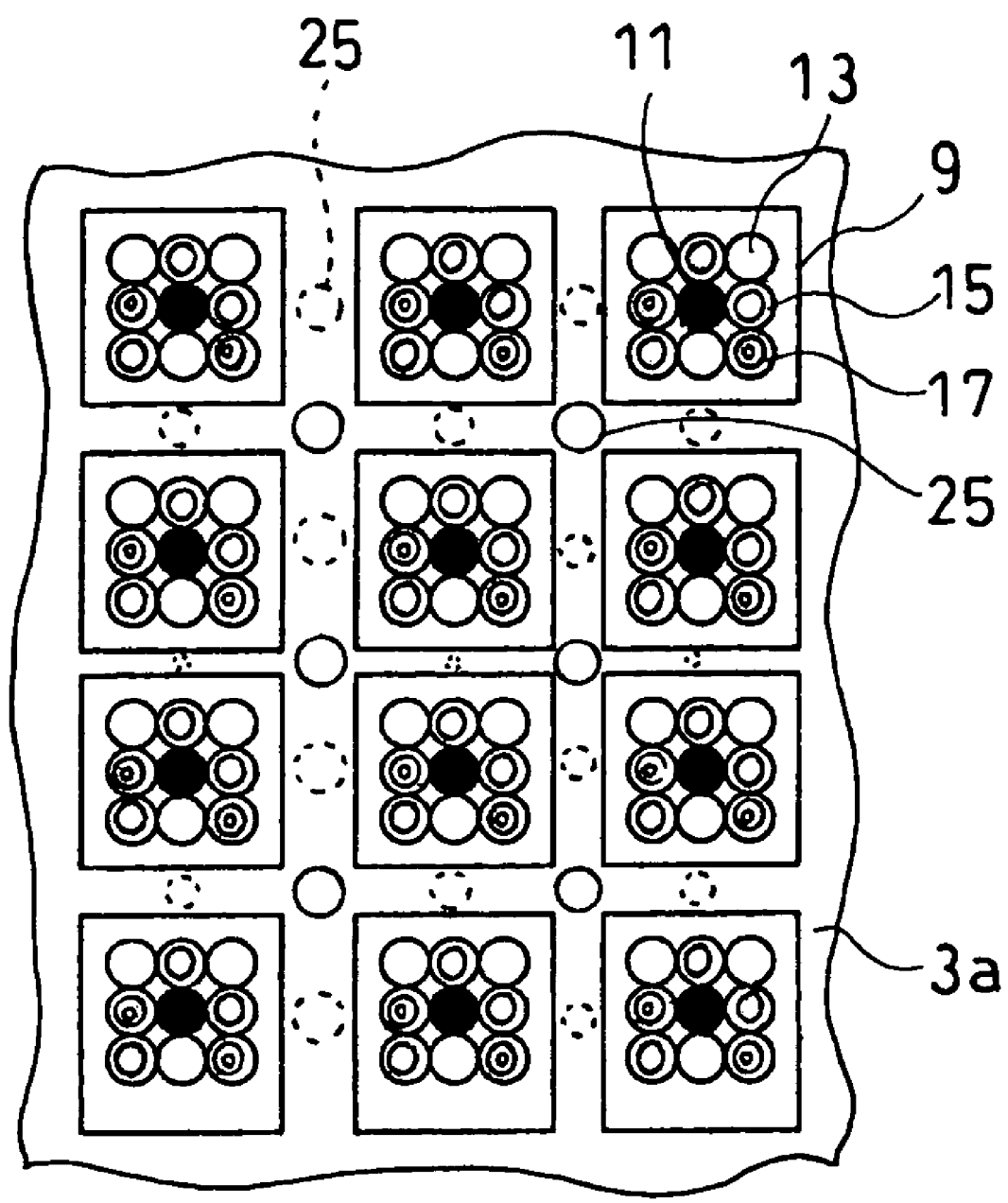
FIG. 3 is a view illustrating a part of an inner surface of a mask.
Figure 4:
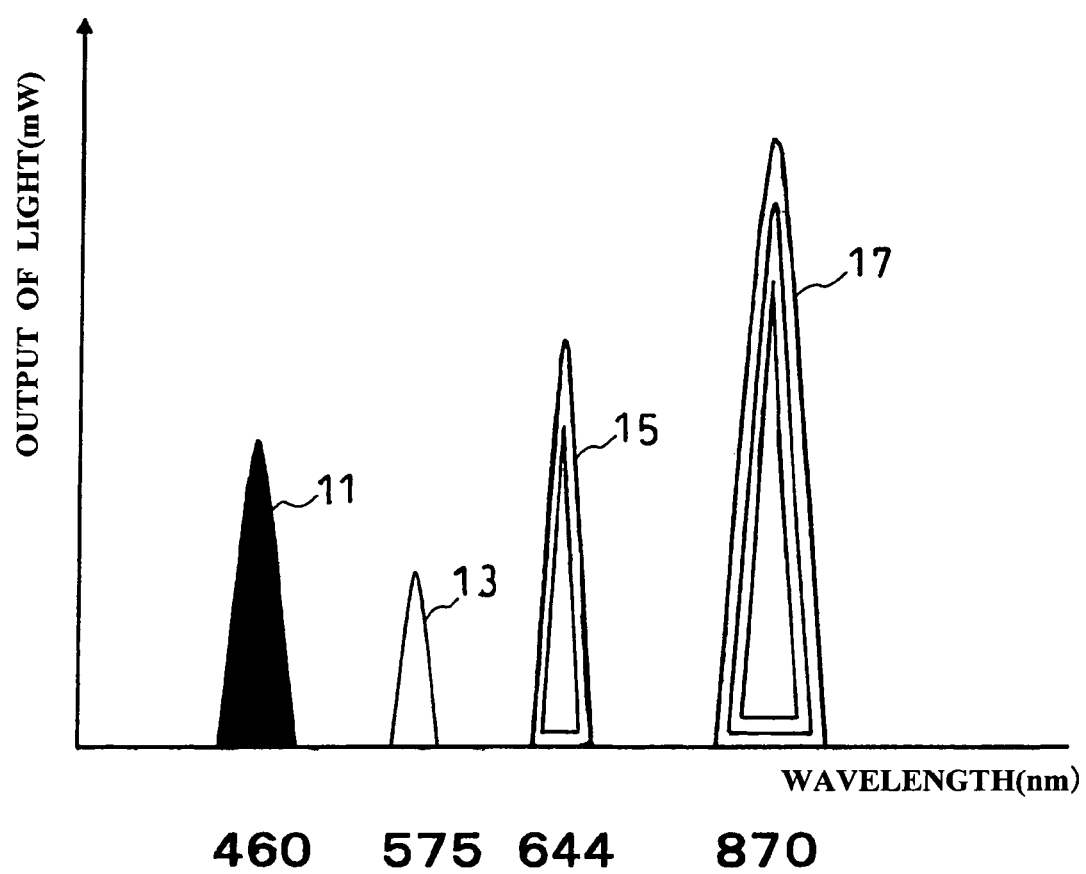
FIG. 4 is a distribution view of LED wavelengths in a light irradiation section.
Figure 5:
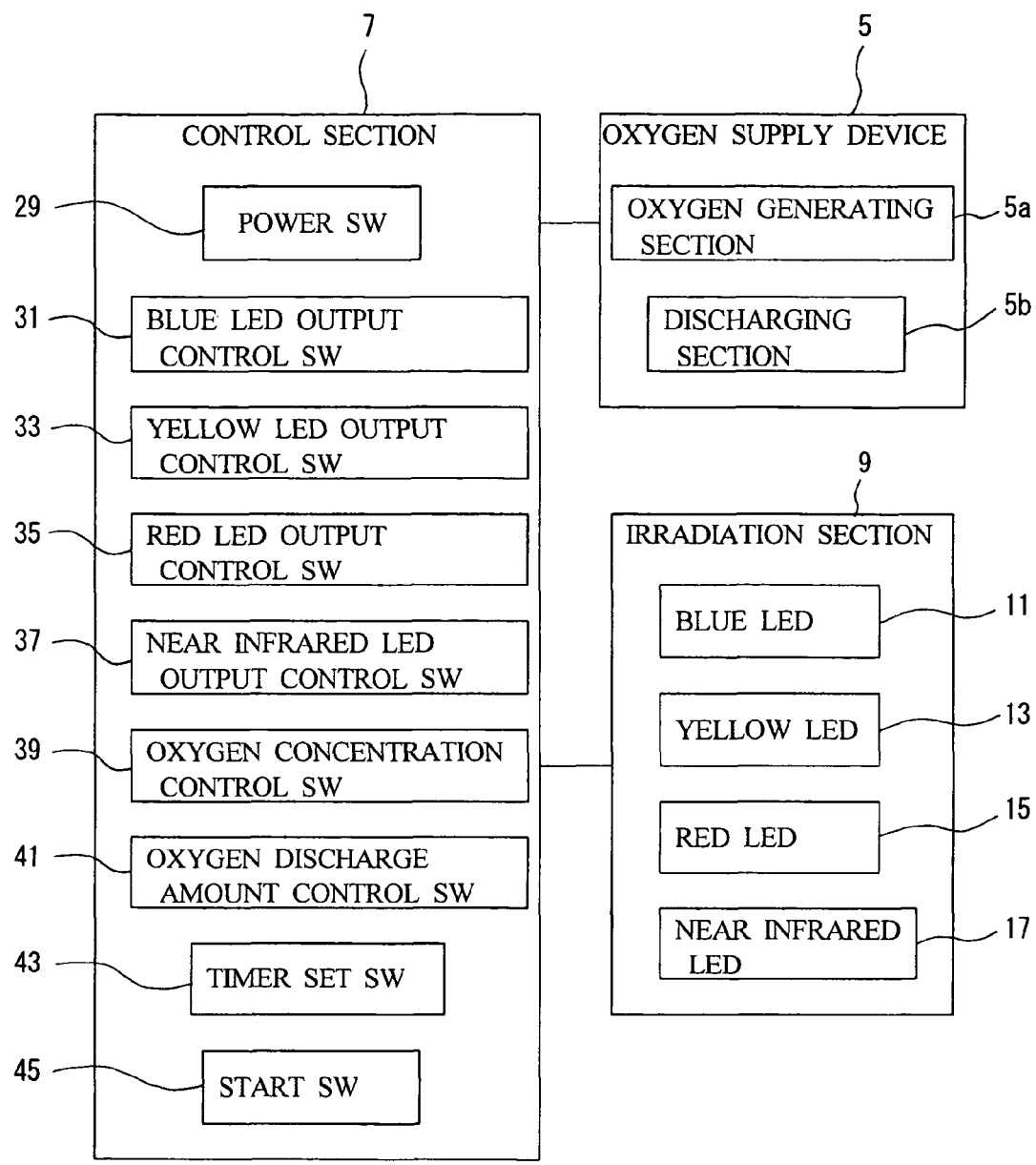
FIG. 5 is a block diagram illustrating a configuration of the beauty device of FIG. 1.

FIG. 1 is a perspective view illustrating an outline of a beauty device according to an embodiment of the present invention; FIG. 2 is a cross sectional view illustrating a mask of a beauty device; FIG. 3 is a view illustrating a part of an inner surface of a mask; FIG. 4 is a distribution view of LED wavelengths in a light irradiation section; and FIG. 5 is a block diagram illustrating a configuration of the beauty device of FIG. 1.

As illustrated in FIG. 1 and FIG. 2, a beauty device 1 of an embodiment of the present invention is used for beauty of a human face A, and includes a mask 3, which covers the face (skin surface) A, an oxygen supply device 5, which supplies oxygen to the mask 3 through a tube 4, and a control section 7.

As illustrated in FIG. 3, multiple light irradiation sections 9, which irradiate the face A with light of multiple predetermined wavelengths (wave arrow in FIG. 2), are formed on an inner surface 3a, which is the face A side, of the mask 3. As illustrated in FIG. 3, the light irradiation sections 9 are arranged in rows and columns at a predetermined distance from one another.

The light irradiation section 9 includes multiple LEDs (Light Emitting Diodes), which have a different wavelength from one another and which are arranged in three rows and three columns. More specifically, as illustrated in FIG. 3 and FIG. 4, the light irradiation section 9 includes a blue LED 11 (a black circle in FIG. 3 and a black triangle in FIG. 4) that emits blue light with an output of 200 mW and a wavelength of 460 nm, yellow LEDs 13 (an open circle in FIG. 3 and an open triangle in FIG. 4) that emit yellow light with an output of 124 mW and a wavelength of 575 nm, red LEDs 15 (a double circle in FIG. 3 and a double triangle in FIG. 4) that emit red light with an output of 274 mW and a wavelength of 644 nm, and near infrared LEDs 17 (a triple circle in FIG. 3 and a triple triangle in FIG. 4) that emit near infrared light with an output of 635 mW and a wavelength of 870 nm. Then, the yellow LEDs 13, the red LEDs 15 and the near infrared LEDs 17 are arranged to surround the blue LED 11 and different LEDs are arranged to be adjacent to one another.

Accordingly, the light wavelengths of adjacent LEDs are produced to be different from one another, making it possible to uniformly and sufficiently interfere light of multiple kinds to perform irradiation and obtain excellent skin beauty effects. Additionally, in FIG. 3, the relationship of arrangement between the yellow LEDs 13 and the red LEDs 15 that surround the blue LED 11 may be suitably changed without being limited to the specific form illustrated in FIG. 3. However, in order to uniformly and sufficiently interfere light of multiple kinds to perform irradiation, LEDs, which are arranged to be adjacent to one another and which have a different wavelength, are desirably used.

Unlike the general LEDs each which emits light through a diffusing lens to increase luminance (light energy in this case is decreased by about 40 volume %), the LEDs 11, 13, 15, 17 used in the embodiment of the present invention are structured in such a manner that the lens is detached from each of the general LEDs and the face A is directly irradiated with light from the LEDs 11, 13, 15, 17, so that light energy is applied to the face A as much as possible. Moreover, each of the LEDs 11, 13, 15, 17 which blinks at random or at predetermined timing by a pulse signal with frequency of 1 Hz to 2 kHz, for example, 20 Hz, 50 Hz, 100 Hz, 200 Hz.

Here, as illustrated in FIG. 5, the oxygen supply device 5 includes an oxygen generating section 5a that generates oxygen and a discharging section 5b that discharges (sends out) the oxygen generated by the oxygen generating section 5a to the tube 4. The oxygen discharged by the discharging section 5b is sent to an internal section of the mask 3 through the tube 4.

In other words, as illustrated in FIG. 2, the internal section of the mask 3 has an oxygen supply passage 19 communicating with the tube 4. The oxygen supply passage 19 includes an introducing passage 21 that introduces the oxygen from the oxygen supply device 5 through the tube 4, and branched passages 23 that are branched into multiple passages from the introducing passage 21. More specifically, as illustrated by a solid line in FIG. 3, outlets of these branched passages 23 are formed between the adjacent up and down light irradiation sections 9 and between the adjacent right and left light irradiation sections 9 to discharge the oxygen to the face A (solid arrow in FIG. 2). The outlet of each of these branched passages 23 is used as an oxygen supply port 25. The oxygen supply port 25 is thus formed between the light irradiation sections 9, thereby making it possible to efficiently supply the oxygen to a light irradiating portion on the face A. Additionally, in the present embodiment, an oxygen supply section 2, which supplies oxygen to the face A, includes the oxygen supply device 5, the tube 4, and the oxygen supply passage 19.

As illustrated in FIG. 5, the oxygen supply device 5 and the light irradiation sections 9 are connected to the output side of the control section 7, and various control of the oxygen supply device 5 and the light irradiation sections 9 is performed by operations to the control section 7.

The control section 7 includes a power switch (SW) 29 of the beauty device 1, a blue LED output control switch 31, a yellow LED output control switch 33, a red LED output control switch 35, and a near infrared LED output control switch 37 each of which controls the output of each of the LEDs, an oxygen concentration control switch 39 that controls concentration of oxygen of the oxygen supply device 5, an oxygen discharge amount control switch 41 that controls an amount of oxygen to be discharged from the oxygen supply device 5, a timer set switch 43 for setting a timer, and a start switch 45 for starting light irradiation by the light irradiation sections 9 and oxygen supply by the oxygen supply section 2 after performing various control.

According to the present embodiment, for example, four output levels of "strong", "medium", "weak", and "no output" can be controlled by operating the respective output control switches 31, 33, 35, and 37. Accordingly, the outputs of LEDs can be controlled depending on the user's skin condition by operating the respective output control switches 31, 33, 35, and 37. For example, the outputs of LEDs are suitably controlled depending on the skin condition while all LEDs 11, 13, 15, 17 are caused to be emitted. Or, the yellow LEDs 13 and the near infrared LEDs 17 are turned off and only the blue LED 11 and the red LEDs 15 are used.

Moreover, the operation of the oxygen concentration control switch 39 makes it possible to control the concentration of oxygen in the range of 30 volume % to 50 volume %. The reason why the concentration of oxygen is set to this range is as follows. Namely, as a result of the experiment, when the concentration is below 30 volume %, much time is required to obtain sufficient skin beauty effects. While, when the concentration exceeds 50 volume %, no difference is found out in the skin beauty effects. Accordingly, the concentration of oxygen is set to 30 volume % to 50 volume %, thereby making it possible to obtain the sufficient skin beauty effects with efficient concentration of oxygen for a short time. Additionally, since the skin beauty effects can be most efficiently obtained when the concentration of oxygen reaches 40 volume % as a result of the experiment, the concentration of oxygen is preferably set to 40 volume % by the oxygen concentration control switch 39.

Furthermore, the operation of the oxygen discharge amount control switch 41 allows a decrease in oxygen when the amount of oxygen, which is discharged from the oxygen supply port 25 formed on the inner surface 3a, which is the face A side, of the mask 3, is large, and an increase in oxygen when the amount of oxygen is small.

Moreover, the timer set switch 43 is one that sets a driving time of each of the oxygen supply device 5 and the light irradiation sections 9 of the beauty device 1. When the timer set switch 43 is operated to set a predetermined time, the driving of the beauty device 1 can be performed for only the predetermined time. For example, when the driving time is set to "5 minutes", the light irradiation from the light irradiation sections 9 and the oxygen supply from the oxygen supply section 2 are stopped after five minutes since the start of the light irradiation and the oxygen supply.

In using the above-structured beauty device 1, the power switch 29 is first turned on to drive the beauty device 1, thereafter, any one of the output control switches 31, 33, 35, 37, the oxygen concentration control switch 39, the oxygen discharge amount control switch 41, and the timer set switch 43 is operated to perform control depending on the skin condition. Then, as illustrated in FIG. 2, after the mask 3 is attached to the face A, the start switch 45 is turned on, thereby light is emitted to the face A from the light irradiation sections 9 on the inner surface 3a, which is the face A side, of the mask 3 and the oxygen is supplied to the face A from the oxygen supply port 25.

Accordingly, irradiation of light with multiple wavelengths (light with two or more wavelengths) from the light irradiation sections 9 stimulates a fibroblast, making it possible to reduce blemishes and wrinkles sufficiently and exert the excellent skin beauty effects. Since no ultraviolet rays are emitted, a fixed skill (with expert knowledge) is not required for using the device, thus allowing safe use of the device at home.

Moreover, in the case where four wavelengths of the LEDs 11, 13, 15, 17 are used, the yellow light, the red light, and the near infrared light are excellent in permeability, and light of four wavelengths of the blue light, the yellow light, the red light and the near infrared light stimulates nerve block to allow an efficient reduction in blemishes and wrinkles. Furthermore, light of multiple kinds can be uniformly and sufficiently interfered to perform irradiation, thereby making it possible to obtain more excellent skin beauty effects such as improvement in pimpled skin, a moisture effect, improvement in a red face, and a reduction in pores of the skin.

In other words, as illustrated in FIG. 2, the internal section of the mask 3 has an oxygen supply passage 19 communicating with the tube 4. The oxygen supply passage 19 includes an introducing passage 21 that introduces the oxygen from the oxygen supply device 5 through the tube 4, and branched passages 23 that are branched into multiple passages from the introducing passage 21. More specifically, as illustrated by a solid line in FIG. 3, outlets of these branched passages 23 are formed between the adjacent up and down light irradiation sections 9 and between the adjacent right and left light irradiation sections 9 to discharge the oxygen to the face A (solid arrow in FIG. 2). The outlet of each of these branched passages 23 is used as an oxygen supply port 25. The oxygen supply port 25 is thus formed between the light irradiation sections 9, thereby making it possible to efficiently supply the oxygen to a light irradiating portion on the face A. Additionally, in the present embodiment, an oxygen supply section 2, which supplies oxygen to the face A (including a mouth of the face A), includes the oxygen supply device 5, the tube 4, and the oxygen supply passage 19.

An experiment using the beauty device 1 of the present embodiment was conducted in the following way. Namely, the beauty device 1 was attached to a subject's skin for five minutes per day during a continuous one week period, and about 20 subjects were subjected to the experiment. Additionally, in the present experiment, the frequency of each of LEDs was about 20 Hz. A questionnaire survey of the result of the experiment was conducted. A questionnaire result was as follows. Namely, 18 subjects answered that blemishes on their skins were eliminated or blemishes and wrinkles were reduced. Furthermore, there were answers that their skin became supple and lustrous after using the beauty device 1 of the present embodiment. Additionally, it had similar results when the frequency of each of LEDs was about 50 Hz, 100 Hz, 200 Hz.

Particularly, in the beauty device 1 of the present embodiment, it was possible to reduce blemishes and wrinkles when the LEDs 11, 13, 15, 17 each of which blinked or emitted light using a pulse signal with frequency of 1 Hz to 2 kHz.

Additionally, it is needless say that the present invention is not limited to the aforementioned embodiment and various modifications may be possible without departing from the broad spirit and scope of the invention.

For example, in the aforementioned embodiment, the oxygen supply port 25 are formed at the position as illustrated by the solid line in FIG. 3. However, the present invention is not limited to the above embodiment. The oxygen supply port 25 may be formed between the adjacent up and down light irradiation sections 9 and between the adjacent right and left light irradiation sections 9 as illustrated by a wave line. Moreover, in place of forming the oxygen supply port 25 between the light irradiation sections 9, the oxygen supply port 25 may be ring-shaped. Then, the ring-shaped oxygen supply port 25 may be formed to cover around each light irradiation section 9 or multiple light irradiation sections 9. Or, the ring-shaped oxygen supply port 25 may be formed along the outer periphery of the face 3a on an inner surface 3a, which is the face A side, of the mask 3. The shape, size, and arranging position are not particularly limited.

Furthermore, in the beauty device 1 of the aforementioned embodiment, the beauty treatment of face A was performed using the mask 3. However, in place of the mask 3, the other covering member may be used. For example, a pad, which covers only a part of the face or a part of the body such as an arm, may be used to perform light irradiation and supply oxygen from an inner surface, which is the face side, of the pad.

Moreover, closing members, which close the light irradiation sections 9 and the oxygen supply port 25, may be provided separately in such a way to close the light irradiation section 9, which does not need light irradiation, among the light irradiation sections 9 and the oxygen supply port 25, which does not need oxygen supply, among the oxygen supply port 25. In this case, for example, light and oxygen can be supplied to only a portion, which is required for beauty care, such as a upper half or a lower half of the face, or a left half or a right half of the face.

Furthermore, in the aforementioned embodiment, both light irradiation by the light irradiation sections 9 and oxygen supply by the oxygen supply section 9 were performed. However, in place of this, the control section 7 may include a selectable switch, which can select only either light irradiation by the light irradiation sections 2 or oxygen supply by the oxygen supply section 2. Then, the beauty device 1 may be driven for either one of the light irradiation and the oxygen supply.

Various embodiments and changes may be made thereunto without departing from the broad spirit and scope of the invention. The above-described embodiment is intended to illustrate the present invention, not to limit the scope of the present invention. The scope of the present invention is shown by the attached claims rather than the embodiment. Various modifications made within the meaning of an equivalent of the claims of the invention and within the claims are to be regarded to be in the scope of the present invention.

What is claimed is:

1. A beauty device comprising:
    a mask arranged to cover a human face;
    a plurality of light irradiation sections arranged on an inner surface of the mask so as to irradiate a skin surface with light of a predetermined wavelength, wherein each light irradiation section includes multiple light emitting diodes operable to emit light at different wavelengths from one another;
    a control section connected to the light irradiation sections, the control section including light emitting diode control switches configured to control each of the light emitting diodes to blink by a pulsed signal; and
    an oxygen supply section for supplying oxygen to the skin surface and to a mouth covered by the mask, the oxygen supply section being arranged on the inner surface of the mask and having an oxygen supply port formed between the light irradiation sections, wherein the oxygen supply section includes an oxygen generating section for generating the oxygen.

2. The beauty device according to claim 1, wherein each light irradiation section includes a blue light emitting diode that emits a blue light, a yellow light emitting diode that emits a yellow light, a red light emitting diode that emits a red light, and a near infrared light emitting diode that emits near infrared light, and the yellow light emitting diode, the red light emitting diode and the near infrared light emitting diode are arranged to surround the blue light emitting diode.

3. The beauty device according to claim 1, wherein oxygen that is supplied by the oxygen supply section has a concentration in a range of 30 volume % to 50 volume %.

4. The beauty device according to claim 1, wherein the oxygen supply section includes an oxygen introducing passage and a plurality of branched passages which branch from the oxygen introducing passage and extend along the inner surface of the mask.

5. The beauty device according to claim 4, wherein the oxygen supply port comprises a plurality of oxygen supply ports, each of the branched passages having an outlet at a respective oxygen supply port.

6. The beauty device according to claim 5, further comprising:
    an oxygen supply tube connected to the mask so as to supply oxygen to the oxygen introducing passage; and
    an oxygen supply device connected to the oxygen supply tube so as to discharge oxygen through the oxygen supply tube to the oxygen introducing passage.

7. The beauty device according to claim 1, further comprising:
    an oxygen supply tube connected to the mask so as to supply oxygen to the oxygen supply section; and
    an oxygen supply device connected to the oxygen supply tube so as to discharge oxygen through the oxygen supply tube to the oxygen supply section.

8. The beauty device according to claim 1, wherein the light emitting diode control switches are configured to control each light emitting diode to blink by a pulsed signal with a frequency of 20 Hz to 2 kHz.

* * * * *